United States Patent
Zhu et al.

(10) Patent No.: US 11,572,594 B2
(45) Date of Patent: Feb. 7, 2023

(54) CHARACTERISTIC SEQUENCE, LABELED PRIMER AND IDENTIFICATION METHOD OF CARYA ILLINOENSIS VARIETY DAVIS

(71) Applicant: Zhejiang Academy of Forestry, Hangzhou (CN)

(72) Inventors: Tangjun Zhu, Hangzhou (CN); Huazheng Peng, Hangzhou (CN); Qunying Jin, Hangzhou (CN); Hualin Ye, Hangzhou (CN)

(73) Assignee: ZHEJIANG ACADEMY OF FORESTRY, Hangzhou (CN)

( * ) Notice: Subject to any disclaimer, the term of this patent is extended or adjusted under 35 U.S.C. 154(b) by 727 days.

(21) Appl. No.: 16/437,512

(22) Filed: Jun. 11, 2019

(65) Prior Publication Data
US 2019/0390287 A1    Dec. 26, 2019

(30) Foreign Application Priority Data
Jun. 26, 2018   (CN) .................... 201810666079.X

(51) Int. Cl.
*C12Q 1/6895* (2018.01)

(52) U.S. Cl.
CPC ....... *C12Q 1/6895* (2013.01); *C12Q 2600/13* (2013.01)

(58) Field of Classification Search
None
See application file for complete search history.

(56) References Cited

PUBLICATIONS

Kaur et al. Characterization of pecan (*Carya illinoensis*) genotypes using RAPD markers. International Journal of Farm Sciences 6(4):77-81. (Year: 2016).*

* cited by examiner

*Primary Examiner* — Samuel C Woolwine
(74) *Attorney, Agent, or Firm* — Muncy, Geissler, Olds & Lowe, P.C.

(57) ABSTRACT

The present invention discloses a highly specific characteristic sequence, molecular specific labeled primer of *Carya illinoensis* variety Davis and applications thereof, and further discloses a method for rapidly identifying *Carya illinoensis* variety Davis. Wherein, the sequence of the molecular specific labeled primer is: upstream primer 5'-TCCTGAAAGCAGCCACAACA-3' (SEQ ID NO:3); downstream primer 5'-GACATGTGTACGAGGTGGTCA-3' (SEQ ID NO:4). The molecular specific labeled primer of the present invention can be used for early identification of the *Carya illinoensis* variety Davis rapidly and easily distinguishing it from other *Carya illinoensis* varieties, providing a strong technical support for the identification of Davis and planting resource protection. The method for rapid identification of the *Carya illinoensis* variety Davis is simple, rapid and accurate, and it is an irreplaceable molecular means for identifying *Carya illinoensis* variety by apparent characteristics.

3 Claims, 1 Drawing Sheet

Specification includes a Sequence Listing.

SEQUENCE LISTING

```
<160> NUMBER OF SEQ ID NOS: 6

<210> SEQ ID NO 1
<211> LENGTH: 400
<212> TYPE: DNA
<213> ORGANISM: Carya illinoensis

<400> SEQUENCE: 1
aattctgtta ggaatttcct gaaagcagcc acaacatatt ggcaaggata tttctatgca      60
aaatagttat tgtgttaaaa taaggtctcc attagatcgt gcacagtaaa gacagtaata     120
tcaaactaaa gtatatatat atacactatt tcttttcttt tccctcacct aattccttca     180
tactaattaa ccacatttac actttttattt gaagaacatt aaaaggttat aatattatca     240
aaattatata atattatact cttttaagg ggttgtttag attcagaaac catcttatct     300
tattttatct catctcatta ttataactgt atcaaatttt tatacaaaat ataatgacca     360
cctcgtacac atgtcttcga attatcatgt tttgtcatgt                            400

<210> SEQ ID NO 2
<211> LENGTH: 359
<212> TYPE: DNA
<213> ORGANISM: Carya illinoensis

<400> SEQUENCE: 2
tcctgaaagc agccacaaca tattggcaag gatatttcta tgcaaaatag ttattgtgtt      60
aaaataaggt ctccattaga tcgtgcacag taaagacagt aatatcaaac taagtatat     120 atatatacac tatttctttt cttttccctc acctaattcc ttcatactaa ttaaccacat     180
ttacactttt atttgaagaa cattaaaagg ttataatatt atcaaaatta tataatatta     240
tactcttttt aaggggttgt ttagattcag aaaccatctt atcttatttt atctcatctc     300
attattataa ctgtatcaaa ttttatacaa aatataatg accacctcgt acacatgtc     359

<210> SEQ ID NO 3
<211> LENGTH: 20
<212> TYPE: DNA
<213> ORGANISM: Artificial Sequence
<220> FEATURE:
<223> OTHER INFORMATION: This sequence is a primer sequence and is
      synthesized.

<400> SEQUENCE: 3
tcctgaaagc agccacaaca                                                  20

<210> SEQ ID NO 4
<211> LENGTH: 21
<212> TYPE: DNA
<213> ORGANISM: Artificial Sequence
<220> FEATURE:
```

```
<223> OTHER INFORMATION: This sequence is a primer sequence and is
      synthesized.

<400> SEQUENCE: 4
gacatgtgta cgaggtggtc a                                              21

<210> SEQ ID NO 5
<211> LENGTH: 20
<212> TYPE: DNA
<213> ORGANISM: Artificial Sequence
<220> FEATURE:
<223> OTHER INFORMATION: This sequence is a primer sequence and is
      synthesized.

<400> SEQUENCE: 5
acctgtaagc agccacaaca                                                20

<210> SEQ ID NO 6
<211> LENGTH: 21
<212> TYPE: DNA
<213> ORGANISM: Artificial Sequence
<220> FEATURE:
<223> OTHER INFORMATION: This sequence is a primer sequence and is
      synthesized.

<400> SEQUENCE: 6
tacatatgta cgaggtggtc a                                              21
```

CHARACTERISTIC SEQUENCE, LABELED PRIMER AND IDENTIFICATION METHOD OF CARYA ILLINOENSIS VARIETY DAVIS

CROSS REFERENCE TO RELATED APPLICATIONS

This application claims priority to Chinese Patent Application No. 201810666079.X, filed on Jun. 26, 2018. The disclosure of each application is incorporated herein by reference in its entirety.

INCORPORATION-BY-REFERENCE OF THE SEQUENCE LISTING

This application includes an electronically submitted sequence listing in .txt format. The .txt file contains a sequence listing entitled "613757 Sequence Listing.txt" created on Jun. 12, 2019 and is 2,381 bytes in size. The sequence listing contained in this .txt file is part of the specification and is hereby incorporated by reference herein in its entirety.

FIELD OF THE INVENTION

The present invention belongs to the technical field of molecular marker identification, and specifically relates to a characteristic sequence, a molecular specific labeled primer and a method for rapidly identifying *Carya illinoensis* variety Davis using the molecular specific labeled primer.

BACKGROUND OF THE INVENTION

*Carya illinoensis* (*Carya illinoënsis* (Wangenh.) K.Koch) is the most economically valuable species of the Juglandaceae *Carya* Nutt., belonging to a typical cross-pollinated plant. In the United States, one of the origins and the central production area of *Carya illinoensis*, about 1,000 *Carya illinoensis* cultivars have been bred and named. The subtropical region of China is a suitable area for *Carya illinoensis*. Up to now, China has introduced *Carya illinoensis* for more than 100 years and there are dozens of varieties commonly used in production.

Davis is a variety selected by Davis Nursery in seedling trees in Mississippi, USA. It was discovered in 1918 and published in 1921. The Davis's tree is tall and grows vigorously. It is a male flower first ripening type, with medium flowering and long female sepals; its fruit is of medium fruit type, with smooth and elliptical shell, sharp tip and round and sharp bottom, about 8.0 g of fruit weight on average. Its nut has a fine ridge in the back a wide main groove, and its base crack is unclear. It is one of the special planting varieties dominated in China, with a large planting area in Zhejiang, Jiangsu, Anhui, etc.

At present, a major problem is low yield and unstable quality in *Carya illinoensis* production areas in China. One of the reasons for this phenomenon is the lack of clear analysis of phylogenetic relationship for the introduced varieties, in addition, some hybrid offspring is named in confusion, so it is difficult to carry out effective parent selection and rational allocation, which is inconvenient for identification, promotion, communication and cultivation of new varieties. At present, *Carya illinoensis* varieties are identified mainly based on morphological characteristics. However, the phenotypic characteristics of different varieties of *Carya illinoensis* are very similar, and the morphological characteristics are susceptible to environmental, climatic and physiological conditions, which easily leads to deviation in subjective identification. Therefore, it is difficult to quickly and accurately identify the *Carya illinoensis* variety by subtle phenotypic differences. Although the identification and phylogenetic relationship analysis methods of *Carya illinoensis* varieties based on SSR molecular markers have been reported at home and abroad, they are cumbersome and the results are unstable. Therefore, the development of some stable and specific DNA fingerprinting markers at the molecular level is a scientific approach to achieve accurate and rapid identification of *Carya illinoensis* varieties.

SUMMARY OF THE INVENTION

It is an object of the present invention to provide a characteristic sequence, a molecular specific labeled primer and a method for rapidly identifying *Carya illinoensis* variety Davis using the molecular specific labeled primer.

In a first aspect, the present invention provides a characteristic sequence of *Carya illinoensis* variety Davis, with the sequence as follows:

```
                                          (SEQ ID NO: 1)
5'-AATTCTGTTAGGAATTTCCTGAAAGCAGCCACAACATATTGGCAAGG

ATATTTCTATGCAAAATAGTTATTGTGTTAAAATAAGGTCTCCATTAGAT

CGTGCACAGTAAAGACAGTAATATCAAACTAAAGTATATATATATACACT

ATTTCTTTTCTTTTCCCTCACCTAATTCCTTCATACTAATTAACCACATT

TACACTTTTATTTGAAGAACATTAAAAGGTTATAATATTATCAAAATTAT

ATAATATTATACTCTTTTTAAGGGGTTGTTTAGATTCAGAAACCATCTTA

TCTTATTTTATCTCATCTCATTATTATAACTGTATCAAATTTTTATACAA

AATATAATGACCACCTCGTACACATGTCTTCGAATTATCATGTTTTGTCA

TGT-3'
```

In a second aspect, the present invention provides a molecular specific labeled primer for identifying *Carya illinoensis* variety Davis.

Preferably, the sequence of the primer is as shown below:

```
Upstream primer:
                                         (SEQ ID NO: 3)
5'-TCCTGAAAGCAGCCACAACA-3';

Downstream primer:
                                         (SEQ ID NO: 4)
5'-GACATGTGTACGAGGTGGTCA-3'.
```

This pair of primers is designed based on PCR. Varieties with large differences in traits are screened from 24 common varieties for reduced-representation sequencing and comparative analysis. More than 1000 pairs of primers are designed for the gene fragments with different sequence differences for screening and verification, in 24 samples. After the preliminary screening and more than three times of repetitive rescreening, the specific DNA fragments of the *Carya illinoensis* variety Davis are obtained, and the fragments are cloned and sequenced. The nucleic acid sequence thereof is shown in SEQ ID NO: 1, and the molecular specific labeled primer is finally obtained. PCR amplification is performed for the *Carya illinoensis* variety using the specific primer. A 359 bp specific fragment (SEQ ID NO: 2) is obtained for Davis only, and no specific fragment is obtained for other *Carya illinoensis* varieties. The nucleotide sequence of the specific fragment is as follows:

(SEQ ID NO: 2)
5'-TCCTGAAAGCAGCCACAACATATTGGCAAGGATATTTCTATGCAAAA

TAGTTATTGTGTTAAAATAAGGTCTCCATTAGATCGTGCACAGTAAAGAC

AGTAATATCAAACTAAAGTATATATATATACACTATTTCTTTTCTTTTCC

CTCACCTAATTCCTTCATACTAATTAACCACATTTACACTTTTATTTGAA

GAACATTAAAAGGTTATAATATTATCAAAATTATATAATATTATACTCTT

TTTAAGGGGTTGTTTAGATTCAGAAACCATCTTATCTTATTTTATCTCAT

CTCATTATTATAACTGTATCAAATTTTTATACAAAATATAATGACCACCT

CGTACACATGTC-3'.

Preferably, a screening method of the molecular specific labeled primer comprises the following steps:

1) Screening multiple varieties with large differences in traits from common *Carya illinoensis* varieties, extracting the genomic DNA of the above varieties, performing reduced-representation sequencing and comparative analysis to obtain SSR-predicted fragments;

2) Carrying out blast analysis after preliminary data assembling of various varieties, then performing precision assembling, selecting 3,893 sequence fragments for primer amplification, and obtaining 473 candidate fragments after sequence alignment with *Juglans regia*, and then designing candidate primers for candidate fragments;

3) carrying out PCR screening of candidate fragments, and selecting DNA bands having polymorphism from the above 24 samples;

4) obtaining a fragment capable of producing a unique characteristic band in the variety Davis after preliminary screening and more than three times of repetitive rescreening, recovering and purifying the band, performing sequencing at both ends using PCR primer, and supplementing unknown base in the middle of the sequence, to obtain a characteristic sequence capable of producing a unique characteristic band in the variety Davis, and finally obtain a molecular specific labeled primer.

Preferably, the principle for primer design in the step 3) is: a primer length of 18-22 bp, Tm temperature range of 56-62 degrees Celsius, and a product length of 150-300 bp.

Preferably, the nucleotide sequence capable of producing a unique characteristic band in the variety Davis in the step 4) is shown in SEQ ID NO:2.

Preferably, the characteristic sequence of the variety Davis obtained in the step 4) is shown in SEQ ID NO:1.

It should be noted that the molecular specific labeled primer of the present invention is limited to the identification of the *Carya illinoensis* variety, that is, the sample to be tested is limited to *Carya illinoensis*.

In a third aspect, the present invention provides a specific DNA fragment obtained from amplification in *Carya illinoensis* variety Davis.

Preferably, the nucleotide sequence of the specific DNA fragment is shown as follows:

(SEQ ID NO: 2)
5'-TCCTGAAAGCAGCCACAACATATTGGCAAGGATATTTCTATGCAAAA

TAGTTATTGTGTTAAAATAAGGTCTCCATTAGATCGTGCACAGTAAAGAC

-continued
AGTAATATCAAACTAAAGTATATATATATACACTATTTCTTTTCTTTTCC

CTCACCTAATTCCTTCATACTAATTAACCACATTTACACTTTTATTTGAA

GAACATTAAAAGGTTATAATATTATCAAAATTATATAATATTATACTCTT

TTTAAGGGGTTGTTTAGATTCAGAAACCATCTTATCTTATTTTATCTCAT

CTCATTATTATAACTGTATCAAATTTTTATACAAAATATAATGACCACCT

CGTACACATGTC-3';

The fragment is 359 bp in size and it is capable of specifically distinguishing Davis from other *Carya illinoensis* varieties.

In a fourth aspect, the present invention provides a method for rapidly identifying *Carya illinoensis* variety Davis.

Preferably, the method comprises the following steps:

1) extracting the genomic DNA of the *Carya illinoensis* variety to be tested;

2) performing PCR amplification using the genomic DNA provided in the step 1) as a template and the molecular specific labeled primer as an amplification primer;

3) carrying out electrophoresis detection of the amplified product of the step 2), determining the *Varia illinoensis* variety to be tested as Davis if a specific DNA fragment of 359 bp appears in the electrophoresis result, and vice versa.

Preferably, the sequence of the molecular specific labeled primer is as follows:

Upstream primer:
5'-TCCTGAAAGCAGCCACAACA-3', as shown in SEQ ID NO: 3;

Downstream primer:
5'-GACATGTGTACGAGGTGGTCA-3', as shown in SEQ ID NO: 4.

Preferably, the nucleotide sequence of the specific DNA fragment is shown in SEQ ID NO: 2.

Preferably, the PCR amplification system is as follows:

The composition of the PCR amplification system per 25 μL is as follows:

| | |
|---|---|
| 10 × PCR Buffer | 2.5 μL |
| 10 mmol/L dNTPs | 2.5 μL |
| 25 mmol/L MgCl2 | 2.5 μL |
| 5 U/μL Taq polymerase | 0.2 μL |
| 10 μM upstream and downstream primers | 1.0 μL each |
| 20 ng/μL template DNA | 3.0 μL |
| ddH2O | 12.3 μL; |

Wherein, the compositions of 10×PCR Buffer: 100 mM Tris-HCl (pH 8.5), 500 mM KCl, 25 mM MgCl2 and 1.0% Triton-X-100, and a solvent of ddH2O.

Or, the composition of the PCR amplification system per 15 μL is as follows:

| | |
|---|---|
| 2 × TsingKE master mix | 7.5 μL |
| 10 μM upstream and downstream primers | 0.6 μL each |
| 20 ng/μL template DNA | 2 μL |
| ddH2O | 4.3 μL; |

Preferably, the PCR amplification conditions are as follows:

After pre-denaturation at 94° C. for 300 s, denaturation at 95° C. for 10 s, annealing at 56° C. for 50 s, extension at 72°

C. for 40 s, a total of 30 cycles, and finally fill-in for 300 s at 72° C.; termination temperature of 4° C.

In the present invention, DNA extraction, PCR reaction system and reaction conditions, and electrophoresis detection can be carried out according to conventional methods in the art. DNA samples from tissues such as leaves, shoots, and fruits can be used as template DNA for identification of variety.

In a fifth aspect, the present invention provides use of a molecular specific labeled primer in identifying *Carya illinoensis* variety Davis.

Preferably, the sequence of the molecular specific labeled primer is as follows:

```
Upstream primer:
                                      (SEQ ID NO: 3)
5'-TCCTGAAAGCAGCCACAACA-3';

Downstream primer:
                                      (SEQ ID NO: 4)
5'-GACATGTGTACGAGGTGGTCA-3'.
```

The above molecular specific labeled primer can be used to identify the *Carya illinoensis* variety Davis quickly and accurately, and distinguish it from other *Carya illinoensis* varieties, providing a strong technical support for the identification of Davis and planting resource protection.

In a sixth aspect, the present invention provides use of a molecular specific labeled primer in preparing a kit for identifying *Carya illinoensis* variety Davis.

Wherein, the sequence of the molecular specific labeled primer is as follows:

```
Upstream primer:
5'-TCCTGAAAGCAGCCACAACA-3', as shown in SEQ ID
NO: 3;

Downstream primer:
5'-GACATGTGTACGAGGTGGTCA-3', as shown in SEQ ID
NO: 4.
```

Preferably, the use of the kit for identifying the *Carya illinoensis* variety Davis comprises the following steps: performing PCR amplification on the sample DNA using the kit with the genomic DNA of the sample to be tested as a template, and carrying out detection of the amplified product by electrophoresis, and if a specific DNA fragment appears, the sample to be tested is Davis.

In a seventh aspect, the present invention provides a kit for identifying *Carya illinoensis* variety Davis, which can be used to identify the *Carya illinoensis* variety Davis conveniently.

Preferably, the kit comprises a molecular specific labeled primer for identifying the *Carya illinoensis* variety Davis.

Preferably, the sequence of the molecular specific labeled primer is as follows:

```
Upstream primer:
                                      (SEQ ID NO: 3)
5'-TCCTGAAAGCAGCCACAACA-3';

Downstream primer:
                                      (SEQ ID NO: 4)
5'-GACATGTGTACGAGGTGGTCA-3'.
```

Preferably, the kit further comprises commonly used reagents for PCR.

Preferably, the commonly used reagents for PCR are PCR Buffer, dNTP Mixture, Taq polymerase, $MgCl_2$, $ddH_2O$.

The present invention can achieve the following beneficial effects:

Firstly, the molecular specific labeled primer of the present invention can be used to rapidly identify the *Carya illinoensis* variety Davis. The method is simple, rapid and accurate, and it is an irreplaceable molecular means for identifying the *Carya illinoensis* variety by apparent characteristics.

Secondly, the method of the present invention has a much higher reliability than the existing SSR marker identification method of the *Carya illinoensis* variety, and it does not require electrophoresis analysis or sequencing at a resolution of 1-2 bp after amplification as that of SSR marker. For this method, ordinary electrophoresis is performed after ordinary PCR, and distinguishing can be made by judging whether or not a specific band is present; in addition, due to high accuracy and specificity, the method of the present invention proposes low requirements for samples. DNA samples of tissues such as leaves and sprouts, etc. can be used for identification of varieties.

DETAILED DESCRIPTION

Figure 1:
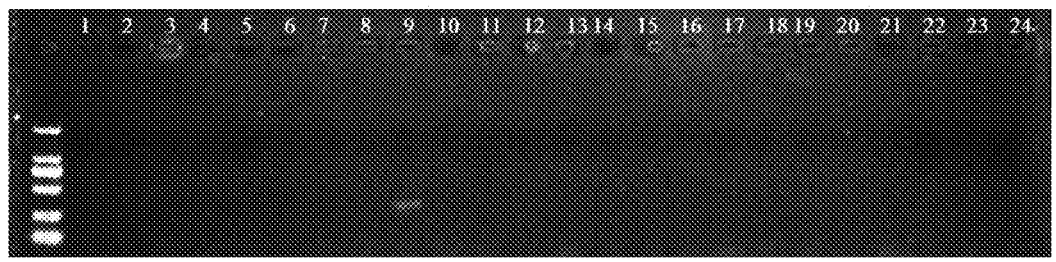
FIG. 1 is the result of PCR amplification of 24 *Carya illinoensis* varieties, where the numbers 1~24 represent the varieties of *Carya illinoensis* as follows: 1. Moore, 2. Dependable, 3. Nacono, 4. Jingzhou No. 1, 5. Van Deman, 6. Sturat 5, 7. Forkert, 8. Desirable, 9. Davis, 10. Elliott, 11. Caddo, 12. Schley, 13. Choctaw, 14. Shaoxing, 15. Wichita, 16. Sumner, 17. Mahan, 18. Gloria Grande, 19. Peruque, 20. Sioux, 21. Pyzner, 22. Pawnee, 23. Osage, 24. Oconee); M is Takara DL2000 marker.

The present invention is further specifically described below with reference to the embodiments. It should be understood that, the present invention is not limited to the embodiments described below, and any form of modifications and/or changes made to the invention are intended to fall within the scope of protection of the present invention.

In the present invention, the method employed in the examples is a general technology in the art unless otherwise specified, and all equipment and raw materials are commercially available or commonly used in the industry. Davis used herein was introduced from the United States in April 2011 by Pecan Breeding & Genetics, Agricultural Research Service, U.S. Dept. of Agriculture, 10200 FM 50 Somerville, Tex. 77879, and it was purchased by Zhejiang Hongyue Seed Co., Ltd, 226 Kaixuan Road, Hangzhou, China, 310020. The trees are planted in Wusheng Village, Fenshui Town, Tonglu County, which belongs to a subtropical monsoon climate zone, 119° 26.9'E, 29° 55.4'N.

Example 1: "Davis" Characteristic Sequence and Preparation of a Molecular Specific Labeled Primer In the present invention, Reduced-Representation Sequencing was performed by RAD (Restriction-site-Associated DNA sequencing), and according to the sequencing results, after a series of analyses and comparisons, the characteristic sequence and molecular specific labeled primer of Davis were obtained. The specific steps were as follows: representative varieties with large differences in traits were selected to extract high-quality DNA, and these DNA samples were digested by a plurality of restriction enzymes, then appropriate enzymes were chosen according to the results of enzyme digestion experiments, to construct a pair-end library with length of 300 to 500 bp, and then the library was sequenced by Illumina HiSeq PE150 to obtain RAD-seq data. In the present invention, EcoRI enzyme was finally chosen, with cleavage site of AATTC).

I. The Extraction of Genomic DNA of *Carya illinoensis* Variety

Twenty-four common varieties were used as samples. 0.05 g of young leaf of *Carya illinoensis* to be tested was taken and thoroughly ground with liquid nitrogen. The genomic DNA was extracted using bioteke novel rapid plant genomic DNA extraction kit according to the operation instructions. After multiple extractions, the genomic DNA extract of the *Carya illinoensis* variety was obtained. The DNA extract was further subjected to 1.5% agarose gel electrophoresis to detect the integrity, purity and concentration. Samples were chosen for subsequent PCR amplification according to the brightness of bands. The DNA extracts were stored in a refrigerator at −20° C. for standby.

It will be appreciated that the extraction of DNA from a sample may employ other methods in the art, and such DNA extraction methods are well known to those skilled in the art.

In the present invention, 24 common varieties were as follows: 1. Moore (*Carya illinoensis* 'Moore'), 2. Dependable (*Carya illinoensis* 'Dependable'), 3. Nacono (*Carya illinoensis* 'Nacono'), 4. Jingzhou No. 1 (*Carya illinoensis* 'Jing Zhou 1'), 5. Van Deman (*Carya illinoensis* 'Van Deman'), 6. Sturat (*Carya illinoensis* 'Sturat'), 7. Forkert (*Carya illinoensis* 'Forkert'), 8. Desirable (*Carya illinoensis* 'Desirable'), 9. Davis (*Carya illinoensis* 'Davis'), 10. Elliott (*Carya illinoensis* 'Elliott'), 11. Caddo (*Carya illinoensis* 'Caddo'), 12. Schley (*Carya illinoensis* 'Schley'), 13. Choctaw (*Carya illinoensis* 'Choctaw'), 14. Shaoxing (*Carya illinoensis* 'Shao Xing'), 15. Wichita (*Carya illinoensis* 'Wichita'), 16. Sumner (*Carya illinoensis* 'Sumner'), 17. Mahan (*Carya illinoensis* 'Mahan'), 18. Gloria Grande (*Carya illinoensis* 'Gloria Grande'), 19. Peruque (*Carya illinoensis* 'Peruque'), 20. Sioux (*Carya illinoensis* 'Sioux'), 21. Pyzner (*Carya illinoensis* Pyzner GP), 22. Pawnee (*Carya illinoensis* 'Pawnee'), 23. Osage (*Carya illinoensis* 'Osage'), 24. Oconee (*Carya illinoensis* 'Oconee').

II. Selection of Characteristic Sequence and Design of Specific PCR Amplification Primers 1. Five varieties of (Van Deman, Moore, Nacono, Davis and Pawnee) with large differences in traits were screened from 24 common varieties, and the reduced-representation sequencing and comparative analysis of the genomic DNA extracted from the five varieties were performed as follows:

(1) DNA samples were digested with EcoRI enzyme to construct a pair-end library with a length ranging from 300 to 500 bp;

(2) Alignment clustering of on Reads1 (the data of the front end after double-ended PE sequencing, i.e., the fragment containing the EcoRI cleavage site AATTC) was performed in each sample;

(3) Internal comparison analysis was performed on the sequence clustering results of each sample, to obtain the information of the heterozygous SNP sites inside the sample;

(4) Sequences between different samples were aligned to search the information of single base difference between individuals, and search for subgroup-specific SNP sites based on sample information;

(5) The double-ended data Reads1 and reads2 were obtained for assembling according to the specific SNP information, to obtain a subgroup-specific genomic fragment.

The specific assembling method:

Cap3 software was used to partially assemble Reads1 and Reads2; a unique Taq (unique Tag) was connected with the longest assembling result (5 "N" added in the middle), to obtain preliminary assembling results; blastn alignment of assembled Tag obtained from a sample with the sequence of other samples was performed by blastn software, and similar sequences were filtered out, with parameter of -evalue: le-5. In addition, before primer design, in order to increase the efficiency of primer amplification, SSR (simple sequence repeat) prediction was performed on the assembling results using MISA (MIcroSatellite identification tool), to eliminate the assembling results containing SSR.

2. After the preliminary data assembling of various varieties, blast analysis was performed to select 3,893 sequence fragments for primer amplification. There were only 473 fragments with sequence homology closest to *Juglans regia* (*Juglans regia*, the variety closest to *Carya illinoensis* in the existing gene bank), which were chosen as the final candidate fragments. Primer pairs were designed. The principle for design of primer pair: a primer length of 18-22 bp, Tm temperature range of 56-62 degrees Celsius, and a product length of 150-300 bp. The primer design was carried out by software Vector NTI9.0. After analyzing the reliability of amplification of primers, including secondary structure, dimer formation, base distribution, etc., 473 pairs of candidate primers were designed.

3. PCR screening was performed for candidate primers, and DNA bands with polymorphism were selected from the above 24 samples, and most of bands did not differ between varieties. Only 80 pairs of primers produced polymorphism in 24 varieties, accounting for ⅙ of all primers.

4. After preliminary screening and more than three times of repetitive rescreening, finally one fragment that produced a unique characteristic band in the Davis variety was obtained, while it was not amplified in the other 23 varieties. The band was recovered and purified, and sequencing at both ends was performed by PCR primer. The sequencing results were conjugated by ContigExpress in the software Vector NTI9.0, and the sequence obtained by resequencing was compared with the previous genome sequencing data, to supplement the unknown bases (represented by NNN previously) in the middle of these candidate sequences. These complete sequences were used as novel candidate scar markers.

Finally, the sequence of primer pairs used for amplification of this fragment was as follows:

```
Upstream primer:
                                      SEQ ID NO: 3
5'-TCCTGAAAGCAGCCACAACA-3',;

Downstream primer:
                                      SEQ ID NO: 4
5'-GACATGTGTACGAGGTGGTCA-3',;
```

The above primers were synthesized by Shanghai Sangon Biotech;

After a large number of screening tests, the characteristic sequence of the *Carya illinoensis* variety Davis was obtained, and the fragment was cloned and sequenced. The nucleotide sequence was as follows:

(SEQ ID NO: 1)
5'-AATTCTGTTAGGAATTTCCTGAAAGCAGCCACAACATATTGGCAAGG

ATATTTCTATGCAAAATAGTTATTGTGTTAAAATAAGGTCTCCATTAGAT

CGTGCACAGTAAAGACAGTAATATCAAACTAAAGTATATATATATACACT

ATTTCTTTTCTTTTCCCTCACCTAATTCCTTCATACTAATTAACCACATT

TACACTTTTATTTGAAGAACATTAAAAGGTTATAATATTATCAAAATTAT

ATAATATTATACTCTTTTTAAGGGGTTGTTTAGATTCAGAAACCATCTTA

TCTTATTTTATCTCATCTCATTATTATAACTGTATCAAATTTTTATACAA

AATATAATGACCACCTCGTACACATGTCTTCGAATTATCATGTTTTGTCA

TGT-3'

In the above screening process, the PCR reaction system and reaction conditions could follow conventional methods in the art. In some preferred embodiments, the composition of the PCR amplification system per 25 μL was as follows:

| 10 × PCR Buffer | 2.5 μL |
| 10 mmol/L dNTPs | 2.5 μL |
| 25 mmol/L MgCl2 | 2.5 μL |
| 5 U/μL Taq polymerase | 0.2 μL |
| 10 μM upstream and downstream primers | 1.0 μL each |
| 20 ng/μL template DNA | 3.0 μL |
| ddH2O | 12.3 μL; |

Wherein, the compositions of 10×PCR Buffer: 100 mM Tris-HCl (pH 8.5), 500 mM KCl, 25 mM MgCl2 and 1.0% Triton-X-100, and a solvent of ddH2O.

Or, the composition of the PCR amplification system per 15 μL was as follows:

| 2 × TsingKE master mix | 7.5 μL |
| 10 μM upstream and downstream primers | 0.6 μL each |
| 20 ng/μL template DNA | 2 μL |
| ddH2O | 4.3 μL; |

The PCR amplification conditions: After pre-denaturation at 94° C. for 300 s, denaturation at 95° C. for 10 s, annealing at 56° C. for 50 s, extension at 72° C. for 40 s, a total of 30 cycles, and finally fill-in for 300 s at 72° C.; termination temperature of 4° C.

Example 2: Verification of "Davis" Molecular Specific Labeled Primer

In order to further verify the accuracy of the molecular specific labeled primer, PCR amplification verification was performed in 24 varieties according to the method described in Example 1.

I. Extraction of Genomic DNA

Genomic DNAs were extracted from young leaves of 24 *Carya illinoensis* varieties according to the process described in Example 1. The 24 *Carya illinoensis* varieties included: 1. Moore, 2. Dependable, 3. Nacono, 4. Jingzhou No. 1, 5. Van Deman, 6. Sturat5, 7. Forkert, 8. Desirable, 9. Davis, 10. Elliott, 11. Caddo, 12. Schley, 13. Choctaw, 14. Shaoxing, 15. Wichita, 16. Sumner, 17. Mahan, 18. Gloria Grande, 19. Peruque, 20. Sioux, 21. Pyzner, 22. Pawnee, 23. Osage, 24. Oconee.

II. PCR Amplification

PCR amplification of the *Carya illinoensis* variety was performed with the specific primer, wherein the composition for PCR reaction (15 μL) was as follows:

| 2 × TsingKE master mix master mix (Tsingke, Beijing) | 7.5 μL |
| 10 μM upstream and downstream primers | 0.6 μL each |
| 20 ng/μL template DNA | 2 μL |
| dd H2O | 4.3 μL; |

The amplification was carried out on a TC-XP amplification system, the amplification conditions: after pre-denaturation at 94° C. for 300 s, denaturation at 95° C. for 10 s, annealing at 56° C. for 50 s, extension at 72° C. for 40 s, a total of 30 cycles, and finally fill-in for 300 s at 72° C.; termination temperature of 4° C.

III. Electrophoresis Detection

3 μL of the PCR amplification product of step 2 was mixed with 1 μL of 0.25% bromophenol blue buffer, and then sample was applied onto a 1.5% agarose gel, and electrophoresis was performed in 1×TAE buffer under a voltage of 5V/cm. At the end of electrophoresis, staining was carried out for 30 minutes in an aqueous solution containing 0.5 μg/mL EB, and then photographed on a Bio-rad gel imaging system Gel Doc. The result was shown in FIG. 1.

As seen from FIG. 1, a clear and stable specific band with molecular weight of 359 bp was amplified only in the No. 9 *Carya illinoensis* variety Davis, but no specific DNA band of 359 bp or other non-target bands were produced in other *Carya illinoensis* varieties. Therefore, the molecular specific labeled primer developed by the present invention can be used for early identification of the *Carya illinoensis* variety Davis, with very high stability and specificity. The Davis-specific DNA fragment obtained by the above screening was sequenced, and the nucleotide sequence of the specific fragment was obtained as follows:

(SEQ ID NO: 2)
5'-TCCTGAAAGCAGCCACAACATATTGGCAAGGATATTTCTATGCAAAA

TAGTTATTGTGTTAAAATAAGGTCTCCATTAGATCGTGCACAGTAAAGAC

AGTAATATCAAACTAAAGTATATATATATACACTATTTCTTTTCTTTTCC

CTCACCTAATTCCTTCATACTAATTAACCACATTTACACTTTTATTTGAA

GAACATTAAAAGGTTATAATATTATCAAAATTATATAATATTATACTCTT

TTTAAGGGGTTGTTTAGATTCAGAAACCATCTTATCTTATTTTATCTCAT

CTCATTATTATAACTGTATCAAATTTTTATACAAAATATAATGACCACCT

CGTACACATGTC-3'.

Example 3: Verification of Other Primers

Figure 2:
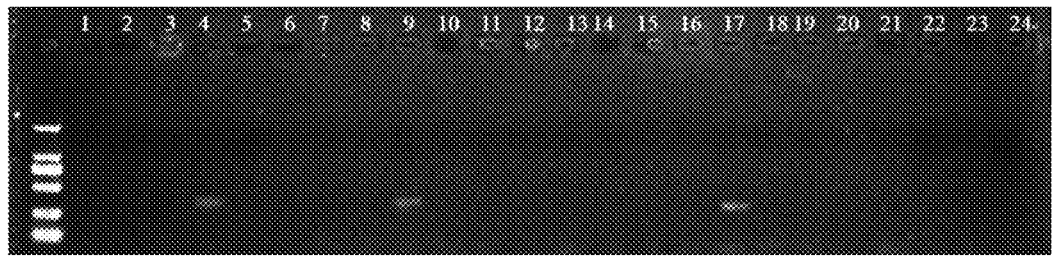
FIG. 2 is the result of PCR amplification of 24 *Carya illinoensis* varieties using other primers.

Another group of primers were used to verify the above 24 varieties. The primer sequences were as follows:

Upstream primer-1:
SEQ ID NO: 5
5'-ACCTGTAAGCAGCCACAACA-3',;

Downstream primer-1:
SEQ ID NO: 6
5'-TACATATGTACGAGGTGGTCA-3',;

As seen from FIG. 2, the 359 bp DNA bands were amplified from *Carya illinoensis* varieties No. 4, No. 9 and No. 17, indicating that the primer group could not distinguish Davis from other varieties and could not be used for specifically screening and identifying Davis.

The invention shown and described herein can be implemented in the absence of any of the elements and limitations specifically disclosed herein. The terms and expressions are used to describe not to limit the invention, and it is not intended to exclude any equivalents of the features shown and described in the use of these terms and expressions, and various variations are possible within the scope of the invention. Therefore, it is to be understood that, although the invention is specifically disclosed by the various embodiments and optional features, modifications and variations of the concepts described herein may be employed by those skilled in the art and these modifications and variations shall fall into the scope of the invention as defined by the appended claims.

The contents of articles, patents, patent applications, and all other documents and electronically available information described or recited herein are hereby incorporated by reference in their entirety as if individually described for reference. Applicants reserve the right to incorporate any and all materials and information from any such article, patent, patent application or other document into this application.

The invention claimed is:

1. A method for rapidly identifying *Carya* illinoensis variety Davis, comprising:
   1) extracting the genomic DNA of the *Carya* illinoensis variety to be tested;
   2) performing PCR amplification using the genomic DNA provided in the step 1) as a template and a pair of primers as an amplification primer set;
   3) carrying out electrophoresis detection of the amplified product of the step 2), determining the *Carya* illinoensis variety to be tested as Davis if a specific DNA fragment of 359 bp appears in the electrophoresis result;
   wherein the pair of primers includes:

```
Upstream primer:
5'-TCCTGAAAGCAGCCACAACA-3', as shown in SEQ ID NO:
3;

Downstream primer:
5'-GACATGTGTACGAGGTGGTCA-3', as shown in SEQ ID
NO: 4.
``` and wherein the specific DNA fragment is shown in SEQ ID NO: 2.

2. The method according to claim 1, wherein the PCR amplification system comprises:
   0.6 μL upstream primer at a concentration of 10 μM; 0.6 μL downstream primer at a concentration of 10 μM; 2.0 μL template DNA at a concentration of 20 ng/μL; 4.3 μL ddH2O; and a total volume of 15 μL; or,
   2.5 μL of 10 ×PCR Buffer; 2.5 μL dNTPs at a concentration of 10 mmol/L; 2.5 μL MgCl2 at a concentration of 25 mmol/L; 0.2 μL Taq polymerase at a concentration of 5 U/μL; 1.0 μL upstream primer at a concentration of 10 μM; 1.0 μL downstream primer at a concentration of 10 μM; 3.0 μL template DNA at a concentration of 20 ng/μL; 12.3 μL ddH2O; and a total volume of 25 μL.

3. The method according to claim 1, wherein the PCR amplification conditions include:
   after pre-denaturation at 94° C. for 300 s, denaturation at 95° C. for 10 s, annealing at 56° C. for 50 s, extension at 72° C. for 40 s, a total of 30 cycles, and finally fill-in for 300s at 72° C.; termination temperature of 4° C.

* * * * *